United States Patent [19]

Connor et al.

[11] Patent Number: 5,489,598

[45] Date of Patent: Feb. 6, 1996

[54] CYTOPROTECTION UTILIZING ARYLTRIAZOL-3-THIONES

[75] Inventors: David T. Connor, Ann Arbor; Janet S. Plummer, Dexter, both of Mich.

[73] Assignee: Warner-Lambert Company, Morris Plains, N.J.

[21] Appl. No.: 255,597

[22] Filed: Jun. 8, 1994

[51] Int. Cl.$^6$ ............................................. A61K 31/41
[52] U.S. Cl. ................................... 514/384; 514/383
[58] Field of Search ........................................... 514/384

[56] References Cited

U.S. PATENT DOCUMENTS

| | | | |
|---|---|---|---|
| 3,514,466 | 5/1970 | Stähle | 260/308 |
| 3,666,771 | 5/1972 | Hoefle et al. | 260/308 R |
| 3,962,237 | 6/1976 | Boyle et al. | 260/247.1 M |
| 4,230,715 | 10/1980 | Albrecht et al. | 424/269 |
| 4,414,221 | 11/1983 | Parsons et al. | 424/269 |
| 4,847,276 | 7/1989 | Yarrington | 514/384 |
| 4,912,095 | 3/1990 | Kane et al. | 548/263.2 |
| 5,100,906 | 3/1992 | Miller | 514/384 |
| 5,143,933 | 9/1992 | Kane et al. | 514/384 |

OTHER PUBLICATIONS

Wallace et al., American Physiological Society, Rapid Communication, pp. G993–G998, 1993.
*The Journal of Immunology*, vol. 144, No. 7, Apr. 1990, Shappell et al., pp. 2702–2711.
*Nature*, vol. 349, Jan. 1991, Watson et al., pp. 164–167.
American Physiological Society, Rapid Communication, Wallace et al., pp. G993–G998 1993.
*Circulation*, vol. 81, No. 1, Jan. 1990, Simpson et al., pp. 226–237.
*The Journal of Immunology*, vol. 150, No. 6, Mar. 1993, Mulligan et al., pp. 2401–2406.
*Gastroenterology*, vol. 100, No. 4, 1991, Wallace et al., pp. 878–883.
*Journal of Leukocyte Biology*, vol. 48, 1990, Rosen, pp. 465–469.
*Journal of Medicinal Chemistry*, vol. 37, No. 1, 1994, Kane et al., pp. 125–132.
*Journal of Medicinal Chemistry*, vol. 33, No. 10, 1990, Kane et al., pp. 2772–2777.
*Journal of Medicinal Chemistry*, vol. 31, No. 6, 1988, Kane et al., pp. 1253–1258.
*Journal of Medicinal Chemistry*, vol. 13, No. 4, 1970, Mhasalkar et al., pp. 672–674.
*Pharmazie*, vol. 48, 1993, Rollas et al., pp. 308–309.
*Journal of Pharmaceutical Sciences*, vol. 58, No. 11, Nov. 1969, Shah et al., pp. 1398–1401.
*Journal of Medicinal Chemistry*, vol. 14, No. 3, 1971, Mhasalkar et al., pp. 260–262.
*Journal of Medicinal Chemistry*, vol. 27, No. 12, 1984, Maxwell et al., pp. 1565–1570.
*J. Heterocyclic Chem.* vol. 29, 1992, Sung et al., pp. 1101–1109.

Primary Examiner—José G. Dees
Assistant Examiner—Dwayne C. Jones
Attorney, Agent, or Firm—Todd M. Crissey; Charles W. Ashbrook

[57] ABSTRACT

5-Aryltriazol-3-thiones are useful for inhibiting adhesion of Mac-1 and thereby providing cytoprotection for diseases mediated by Mac-1 adhesion.

11 Claims, No Drawings

CYTOPROTECTION UTILIZING ARYLTRIAZOL-3-THIONES

BACKGROUND OF THE INVENTION

This invention relates to a method of treatment utilizing aryltriazol-3-thiones. We have discovered these compounds effectively inhibit the integrin known as Mac-1, and thereby are useful as cytoprotective agents against disease states mediated by Mac-1.

Leukocyte-endothelial interactions are involved in the pathogenesis of various inflammatory diseases. In an immune or inflammatory response, circulating neutrophils interact with the endothelium via their adhesion molecules. The adherence of the neutrophil to the endothelium, and the subsequent transendothelium migration to the site of injury or infection, is the normal host response. Unfortunately, in various disease states such a response can become too aggressive; the influx of neutrophils can cause damage to tissue, thereby causing chronic inflammation.

Cell adhesion molecules can be classified in a number of families, three of which are the integrins, the immunoglobulins, and the selectins. The integrins can be found on leukocytes and platelets. They bind to the immunoglobulin family on blood vessel endothelial cells.

The leukocyte adhesion molecule Mac-1 (CD11b/CD18) is a heterodimeric glycoprotein expressed on the plasma membrane of neutrophils and monocytes. Mac-1 is a member of the $\beta_2$ subfamily of integrins. Interaction of upregulated Mac-1 on stimulated neutrophils with its ligands on endothelial cells plays an important role in the pathogenesis of numerous inflammatory disease states. The response of the neutrophil in host defense function depends on this type of adherence. The inflammatory response depends on neutrophil influx to the site of infection or injury. A rational target for therapeutic intervention thus is to inhibit the adhesion process. Drugs which inhibit the adhesion of leukocytes to the endothelium could be used as therapeutic agents in such conditions as ischemia, reperfusion, transplant rejection, ulcerative colitis, inflammatory bowel disease, multiple sclerosis, rheumatoid arthritis, and NSAID-induced gastropathy.

The binding of the denatured protein known as keyhole limpet hemocyanin (KLH) to human and canine neutrophils has been shown to be Mac-1 specific (*J. Immunol.*, 144(7):2702–2711, April 1990). The binding of stimulated neutrophils (with fMLP) to KLH can be blocked with antibodies to Mac-1. An inhibition of the adhesion process using monoclonal antibodies has been shown to inhibit the inflammatory response in a model of lung injury (Rosen H., *J. Leuk. Biol.*, 48:465 (1990); Mulligan M. S., et al., *J. Immunol.*, 150:2401–2406 (1993)), and a canine model of myocardial ischemia/reperfusion injury (Simpson P. J., et al., *Circulation*, 81:226–237 (1990)). We have now discovered that small molecular weight aryltriazol-3-thiones also inhibit the adhesion of Mac-1 to KLH coated plates.

The role of leukocyte adhesion molecules in NSAID gastropathy has been well documented by John Wallace, et al., *Gastroenterology*, 100:878–883 (1991); *Am. J. Physiol.*, 259 (1990); G462–G467). Neutrophil adherence to the endothelium is a critical pathogenic event in models of gastrointestinal ulceration. Anti-CD18 monoclonal antibody markedly reduced the severity of damage induced by indomethacin in the rat. Similar results were obtained with anti-ICAM. While these monoclonal antibodies have been found to inhibit the adhesion of Mac-1, the need continues to find small molecular weight organic molecules which are also effective. We have now found that the aryltriazoles described below inhibit Mac-1 adhesion, and thereby are effective in treating diseases medicated thereby.

An object of this invention is thus to provide a method for inhibiting the adhesion of Mac-1 in diseases mediated by such molecule. A further object is a method of treatment of diseases including NSAID-induced gastritis and ulceration, ischemia, reperfusion, ulcerative colitis, inflammatory bowel disease, rheumatoid arthritis, and multiple sclerosis. In general, this invention provides a method of providing cytoprotection by administering an aryltriazol-3-thione.

SUMMARY OF THE INVENTION

This invention provides a method of providing cytoprotection by inhibiting the integrin Mac-1 comprising administering to a subject in need of such treatment a Mac-1 inhibitory amount of a compound defined by Formula I

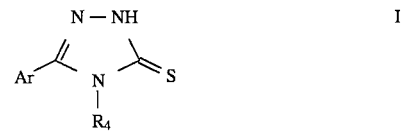

wherein Ar is phenyl, pyridyl, naphthyl and fluorenyl, and $R_4$ is hydrogen, amino, alkylamino, dialkylamino, hydroxy, alkyl, alkenyl, cycloalkyl, phenyl, substituted phenyl, benzyl or substituted benzyl, and the pharmaceutically acceptable acid addition salts thereof. The thiones are tautomeric with the corresponding thiols.

A preferred embodiment comprises administering a compound of Formula II

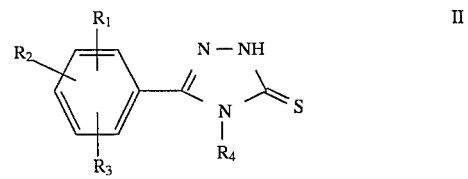

wherein $R_1$, $R_2$, and $R_3$ are substituent groups as defined below. In the above formula:

Ar is phenyl, substituted phenyl, pyridyl, substituted pyridyl, naphthyl, substituted naphthyl, fluorenyl or substituted fluorenyl, wherein the substituent groups are 1, 2, or 3 groups selected from $R_1$, $R_2$, and $R_3$;

$R_1$, $R_2$, and $R_3$ independently are hydrogen, hydroxy, $C_1$–$C_4$ alkyl, $C_1$–$C_4$ alkoxy, $C_1$–$C_4$ alkylthio, nitro, amino, $C_1$–$C_4$ alkylamino, di-$C_1$–$C_4$ alkylamino, $C_1$–$C_4$ alkanoylamino, phenoxy, trifluoromethyl, 1-pyrrolo, —$N(CH_2)_n$ where n is 3, 4, 5, or 6, or halo;

$R_4$ is hydrogen, $C_1$–$C_4$ alkyl, $C_2$–$C_4$ alkenyl, $C_3$–$C_6$ cycloalkyl, amino, hydroxy, $C_1$–$C_4$ alkylamino, di-$C_1$–$C_4$ alkylamino, phenyl or substituted phenyl, benzyl or substituted benzyl, and the pharmaceutically acceptable acid addition salts thereof.

In a preferred method of inhibiting Mac-1, the compound administered is selected from the group consisting of:

5-(4-aminophenyl)-4-ethyl-2,4-dihydro-[1,2,4]triazol-3-thione 5-(2,6-dimethoxyphenyl)-4-ethyl-2,4-dihydro-[1,2,4]triazol-3-thione 5-(4-hydroxyphenyl)-4-ethyl-2,4-dihydro-[1,2,4]triazol-3-thione 5-(2-hydroxyphenyl)-4-ethyl-2,4-dihydro-[1,2,4]triazol-3-thione 5-(2-amino-5-chlorophenyl)-4-cyclopropyl-2,4-dihydro-[1,2,4]triazol-3-thione
5-(2-amino-4,5-dimethoxyphenyl)-4-ethyl-2,4-dihydro-[1,2,4]triazol-3-thione
5-(2-aminopyridin-3-yl)-4-ethyl-2,4-dihydro-[1,2,4]triazol-3-thione
5-(2-amino-5-methoxyphenyl)-4-tert.-butyl-2,4-dihydro-[1,2,4]triazol-3-thione
5-(2-amino-3-methoxyphenyl)-4-ethenyl-2,4-dihydro-[1,2,4]triazol-3-thione
5-(4-methoxyphenyl)-4-ethyl-2,4-dihydro-[1,2,4]triazol-3-thione
5-(2,4-chlorophenyl)-4-ethyl-2,4-dihydro-[1,2,4]triazol-3-thione
4-(3-buten-1-yl)-5-phenyl-2,4-dihydro-[1,2,4]triazol-3-thione
5-(2-methoxyphenyl)-4-ethyl-2,4-dihydro-[1,2,4]triazol-3-thione
5-(4-phenoxyphenyl)-4-ethyl-2,4-dihydro-[1,2,4]triazol-3-thione
5-(3,4-dimethoxyphenyl)-4-ethyl-2,4-dihydro-[1,2,4]triazol-3-thione
5-(3,4-dimethoxyphenyl)-2,4-dihydro-[1,2,4]triazol-3-thione
5-(2-methoxyphenyl)-2,4-dihydro-[1,2,4]triazol-3-thione
4-ethyl-5-(9-fluoren-9-yl)-2,4-dihydro-[1,2,4]triazol-3-thione
5-(7-bromo-3-hydroxy-2-naphthyl)-4-ethyl-2,4-dihydro-[1,2,4]triazol-3-thione
5-(3-ethylamino-2-naphthyl)-4-ethyl-2,4-dihydro-[1,2,4]triazol-3-thione
5-(2-methylphenyl)-2,4-dihydro-4-phenyl-3H-1,2,4-triazol-3-thione
2,4-dihydro-4,5-diphenyl-3H-1,2,4-triazol-3-thione
5-(2-methoxyphenyl)-2,4-dihydro-4-phenyl-3H-1,2,4-triazol-3-thione
2 4-dihydro-5-phenyl-4-(phenylmethyl)-3H-1,2,4-triazol-3-thione
5-(3,4-dimethoxyphenyl)-2,4-dihydro-4-phenyl-3H-1,2,4-triazol-3-thione
5-(4-hydroxyphenyl)-2,4-dihydro-4-phenyl-3H-1,2,4-triazol-3-thione
5-(3-methoxyphenyl)-2,4-dihydro-4-phenyl-3H-1,2,4-triazol-3-thione
5-(4-hydroxyphenyl)-2,4-dihydro-4-phenylmethyl-3H-1,2,4-triazol-3-thione
5-(4-nitrophenyl)-2,4-dihydro-4-phenyl-3H-1,2,4-triazol-3-thione
5-(4-aminophenyl)-2,4-dihydro-4-phenyl-3H-1,2,4-triazol-3-thione
5-(3,4-dimethoxyphenyl)-2,4-dihydro-4-methyl-3H-1,2,4-triazol-3-thione
5-(4-trifluoromethylphenyl)-2,4-dihydro-4-phenyl-3H-1,2,4-triazol-3-thione
1,2-dihydro-5-phenyl-3H-1,2,4-triazol-3-thione
5-(3-aminophenyl)-2,4-dihydro-4-phenyl-3H-1,2,4-triazol-3-thione
5-(2-aminophenyl)-4-ethyl-2,4-dihydro-[1,2,4]triazol-3-thione
5-(2-aminomethylphenyl)-4-ethyl-2,4-dihydro-[1,2,4]triazol-3-thione
5-(2-N,N-dimethylaminophenyl)-2,4-dihydro-4-methyl-[1,2,4]triazol-3-thione
4-amino-5-(2-aminophenyl)-2,4-dihydro-3H-1,2,4-triazol-3-thione

DETAILED DESCRIPTION OF THE INVENTION

The compounds to be utilized in the method of this invention are generally known in the art. Kane, et al., describes the synthesis and antidepressant and anticonvulsant use of various of the compounds in U.S. Pat. Nos. 4,912,095 and 5,143,933, which are incorporated herein by reference. Albrecht, et al., describes the antisecretory activity of such compounds in U.S. Pat. No. 4,230,715, also incorporated herein by reference.

The compounds to be employed can be synthesized by any of several processes, all of which are well known in the art. A typical process comprises reacting an arylcarboxylic acid ester (e.g., Ar—COOCH$_3$) with hydrazine to produce an arylhydrazide (Ar—CONHNH$_2$), reacting the arylhydrazide with an thioisocyanate of the formula R$_4$NCS to produce a thiosemicarbazide of the formula Ar—CONHNHCSNHR$_4$, and then effecting ring closure by reaction with a base such as sodium hydroxide or sodium bicarbonate.

In the above formula, Ar means phenyl, pyridyl, naphthyl, and fluorenyl. Each of the aryl groups can be substituted with 1, 2, or 3 groups selected from $C_1$–$C_4$ alkyl, $C_1$–$C_4$ alkoxy, $C_1$–$C_4$ alkylthio, nitro, amino, $C_1$–$C_4$ alkylamino, di-$C_1$–$C_4$ alkylamino, $C_1$–$C_4$ alkanoylamino, phenoxy, trifluoromethyl, 1-pyrrolo, —N(CH$_2$)$_n$ where n is 3, 4, 5, or 6, or halo. "$C_1$–$C_4$ Alkyl" groups include methyl, ethyl, isopropyl, and tert.-butyl. Typical "$C_1$–$C_4$ alkoxy" groups include methoxy, n-propoxy, isobutoxy, and the like. "$C_1$–$C_4$ Alkylthio" includes methylthio and isobutylthio. "$C_1$–$C_4$ Alkylamino" includes methylamino, isopropylamino, n-butylamino, and di-$C_1$–$C_4$ alkylamino includes methylethylamino, diethylamino, methyl-n-butylamino and the like. "$C_1$–$C_4$ Alkanoylamino" includes formamido, acetamido, propionamido and the like. "Halo" means fluoro, chloro, bromo, and iodo, and preferably is fluoro or chloro.

R$_4$ in the above formula includes $C_1$–$C_4$ alkyl such as methyl and n-butyl, $C_2$–$C_4$ alkenyl such as ethenyl, 2-propenyl, and 2-butenyl and $C_3$–$C_6$ cycloalkyl such as cyclopropyl, cyclopentyl, and cyclohexyl.

The synthesis of typical compounds to be employed in the method of this invention is illustrated by the following examples.

EXAMPLE 1

A. Preparation of 4-Aminobenzoic acid hydrazide

A mixture of 5.0 g (33 mmol) of 4-aminomethylbenzoate and 4.5 mL of hydrazine in 8 mL of absolute ethanol was heated at reflux for 24 hours. The mixture was cooled to 24° C. and filtered. The precipitate was washed with ethanol and dried under vacuum to provide 4.5 g (90%) of 4-aminobenzoic acid hydrazide, mp 226°–228° C.

B. Preparation of 1-(4-Aminobenzoyl)-4-ethylthiosemicarbazide

A mixture of 4.5 g (29.8 mmol) of 4-aminobenzoic acid hydrazide and 2.6 mL of ethylthioisocyanate in 15 mL of acetonitrile was heated at reflux for 3 hours. The solution was cooled to 24° C., and the precipitate was collected by filtration and dried under vacuum to afford 7.0 g of 1-(4-aminobenzoyl)-4-ethylthiosemicarbazide, mp 113°–115° C.

C. Synthesis of 5-(4-Aminophenyl)-4-ethyl-2,4-dihydro-[1,2,4]triazol-3-thiones

A mixture of 3.0 g (12.6 mmol) of 1-(4-aminobenzoyl)-4-ethylthiosemicarbazide and 4.8 mL of 2N sodium hydroxide in 38 mL of water was heated at reflux for 2 hours. The reaction mixture was cooled to 24° C. and diluted with glacial acetic acid to pH=3. The precipitate which formed was collected by filtration and washed with ethyl acetate-:methanol (1:1 v/v) to provide 2.28 g (82%) of 5-(4- aminophenyl)-4-ethyl-2,4-dihydro-[1,2,4]triazol-3-thione, mp 240°–250° C.

EXAMPLES 2–37

By following the general procedure of Example 1, an arylcarboxylic acid ester was reacted with hydrazine to produce the corresponding hydrazide, which was reacted with thioisocyanate to provide an arylthiosemicarbazide, which is reacted with a base to effect cyclization to the named aryltriazol-3-thiones.

| Example | |
|---|---|
| 2 | 5-(4-aminophenyl)-4-ethyl-2,4-dihydro-[1,2,4]triazol-3-thione; mp 240-250° C. |
| 3 | 5-(2,6-dimethoxyphenyl)-4-ethyl-2,4-dihydro-[1,2,4]triazol-3-thione; mp 226–227°C. |
| 4 | 5-(4-hydroxyphenyl)-4-ethyl-2,4-dihydro-[1,2,4]triazol-3-thione; mp 196–199° C. |
| 5 | 5-(2-hydroxyphenyl)-4-ethyl-2,4-dihydro-[1,2,4]triazol-3-thione; mp 237–246° C. |
| 6 | 5-(2-amino-5-chlorophenyl)-4-ethyl-2,4-dihydro-[1,2,4]triazol-3-thione; mp 211–212° C. |
| 7 | 5-(2-amino-4,5-dimethoxyphenyl)-4-ethyl-2,4-dihydro-[1,2,4]triazol-3-thione; mp 174–177° C. |
| 8 | 5-(2-aminopyridin-3-yl)-4-ethyl-2,4-dihydro-[1,2,4]triazol-3-thione; mp 216–218° C. |
| 9 | 5-(2-amino-5-methoxyphenyl)-4-ethyl-2,4-dihydro-[1,2,4]triazol-3-thione; mp 158–160° C. |
| 10 | 5-(2-amino-3-methoxyphenyl)-4-ethyl-2,4-dihydro-[1,2,4]triazol-3-thione; mp 140–141° C. |
| 11 | 5-(4-methoxyphenyl)-4-ethyl-2,4-dihydro-[1,2,4]triazol-3-thione; mp 176-177° C. |
| 12 | 5-(2,4-chlorophenyl)-4-ethyl-2,4-dihydro-[1,2,4]triazol-3-thione; mp 193–194° C. |
| 13 | 4-ethyl-5-phenyl-2,4-dihydro-[1,2,4]triazol-3-thione; mp 136-137° C. |
| 14 | 5-(2-methoxyphenyl)-4-ethyl-2,4-dihydro-[1,2,4]triazol-3-thione; mp 171–172° C. |
| 15 | 5-(4-phenoxyphenyl)-4-ethyl-2,4-dihydro-[1,2,4]triazol-3-thione; mp 145–147° C. |
| 16 | 5-(3,4-dimethoxyphenyl)-4-ethyl-2,4-dihydro-[1,2,4]triazol-3-thione; mp 166–168° C. |
| 17 | 5-(3,4-dimethoxyphenyl)-2,4-dihydro-[1,2,4]triazol-3-thione; mp 298–300° C. |
| 18 | 5-(2-methoxyphenyl)-2,4-dihydro-[1,2,4]triazol-3-thione; mp 244–245° C. |
| 19 | 4-ethyl-5(9-fluoren-9-yl)-2,4-dihydro-[1,2,4]triazol-3-thione; mp 172-173° C. |
| 20 | 5-(7-bromo-3-hydroxy-2-naphthyl)-4-ethyl-2,4-dihydro-[1,2,4]triazol-3-thione; mp 245-248° C. |
| 21 | 5-(3-amino-2-naphthyl)-4-ethyl-2,4-dihydro-[1,2,4]triazol-3-thione; mp 225–228° C. |
| 22 | 5-(2-methylphenyl)-2,4-dihydro-4-phenyl-3H-[1,2,4]-triazol-3-thione; mp 209–210° C. |
| 23 | 2,4-dihydro-4,5-diphenyl-3H-[1,2,4]-triazol-3-thione; mp 287–288° C. |
| 24 | 5-(2-methoxyphenyl)-2,4-dihydro-4-phenyl-3H-[1,2,4]-triazol-3-thione; mp 248–250° C. |
| 25 | 2,4-dihydro-5-phenyl-4-(phenylmethyl)-3H-[1,2,4]-triazol-3-thione; mp 185–186° C. |
| 26 | 5-(3,4-dimethoxyphenyl)-2,4-dihydro-4-phenyl-3H-1,2,4-triazole-3-thione; mp 224–225° C. |
| 27 | 5-(4-hydroxyphenyl)-2,4-dihydro-4-phenyl-3H-[1,2,4]-triazol-3-thione; mp 261–271° C. |
| 28 | 5-(3-methoxyphenyl)-2,4-dihydro-4-phenyl-3H-[1,2,4]-triazol-3-thione; mp 212–214° C. |
| 29 | 5-(4-hydroxyphenyl)-2,4-dihydro-4-phenylmethyl-3H-[1,2,4]-triazol-3-thione; mp 236–238° C. |
| 30 | 5-(4-nitrophenyl)-2,4-dihydro-4-phenyl-3H-[1,2,4]-triazol-3-thione; mp 264–266° C. |
| 31 | 5-(4-aminophenyl)-2,4-dihydro-4-phenyl-3H-[1,2,4]-triazol-3-thione; mp 288–290° C. |
| 32 | 5-(3,4-dimethoxyphenyl)-2,4-dihydro-4-methyl-3H-[1,2,4]-triazol-3-thione; mp 208–209° C. |
| 33 | 5-(4-methoxyphenyl)-2,4-dihydro-4-phenyl-3H-[1,2,4]-triazol-3-thione; mp 288–289° C. |
| 34 | 1,2-dihydro-5-phenyl-3H-[1,2,4]-triazol-3-thione; mp 258–261° C. |
| 35 | 5-(aminophenyl)-2,4-dihydro-4-phenyl-3H-[1,2,4]-triazol-3-thione; mp 250° C. (decomp) |
| 36 | 5-(2-aminophenyl)-4-ethyl-2,4-dihydro-[1,2,4]triazol-3-thione; mp 150-153° C. |
| 37 | 5-(2-methylaminophenyl)-4-phenyl-2,4-dihydro-[1,2,4]triazol-3-thione; mp 255–256° C. |

EXAMPLE 38

5-(2-Aminophenyl)-2,4-dihydro-4-methyl-4H-[1,2,4]-triazol-3-thione

A. Preparation of 5-(2-Aminophenyl)-2-thio-1,3,4-oxadiazole

To a stirred solution of 60 g of 2-aminobenzoic acid hydrazide in 500 mL of ethanol was added a solution of 22.2 g of potassium hydroxide in 50 mL of water. The mixture was heated at reflux while 27 mL of carbon disulfide was added dropwise over 30 minutes. The mixture was cooled to 24° C. and concentrated to 60 mL by evaporation under reduced pressure. The concentrate was added to 200 mL of water containing 100 mL of glacial acetic acid. The acidic solution was adjusted to pH 5 by addition of ammonium hydroxide. The precipitate which formed was collected by filtration and air dried to give 5-(2-aminophenyl)-2-thio-1,3,4-oxadiazoles.

B. Synthesis of 5-(2-Aminophenyl)-2,4-dihydro-4-methyl-4H-[1,2,4]triazol-3-thione A mixture of 15.0 g of 5-(2-aminophenyl)-2-thio-1,3,4-oxadiazole in 40 mL of 40% aqueous methylamine was heated in a bomb at 120° C. for 5 hours. The bomb was cooled and the solution was removed. The solution was heated on a steam bath to remove the remaining methylamine. The solution was then cooled to 24° C. and neutralized by addition of acetic acid. The mixture was added to 50 mL of diisopropyl ether, and the product formed as an oil, which was then crystallized from ethyl acetate to give 5-(2-aminophenyl)-2,4-dihydro-4-methyl-4H-[1,2,4]triazol-3-thiones, mp 164°–165° C.

EXAMPLE 39

4-Amino-5-(2-aminophenyl)-2,4-dihydro-3H-[1,2,4]-triazol-3-thione 5-(2-Aminophenyl)-2-thio-1,3,4-oxadiazole (13.0 g from Example 38A above) was dissolved in 20 mL of 85% aqueous hydrazine and the solution was heated at reflux for 2 hours. The solution was cooled to 24° C., diluted with 30 mL of water, and neutralized by addition of glacial acetic acid. The solid precipitate was collected by filtration and recrystallized from ethanol to provide 7.0 g of 4-amino-5-(2-aminophenyl)-2,4-dihydro-3H-[1,2,4]triazol-3-thione, mp 191°–192° C.

EXAMPLE 40

5-(2-Acetamidophenyl)-2,4-dihydro-4-ethyl-1H-[1,2,4]triazol-3-thione

A solution of 0.25 g of 5-(2-aminophenyl)-2,4-dihydro-4-ethyl-1H-[1,2,4]triazol-3-thione and 0.13 mL of acetic anhydride in 1.5 mL of tetrahydrofuran and 0.7 mL of water was stirred at 24° C. for 4 hours. The solution was diluted with 25 mL of ethyl acetate, washed with brine, and dried over $MgSO_4$. The mixture was filtered and the filtrate was concentrated to dryness and then dissolved in 20 mL of 1N sodium hydroxide. The aqueous mixture was extracted twice with 20 mL portions of ethyl acetate. The extracts were combined, washed with brine, dried, and concentrated to dryness to give a solid. The solid was triturated with ethyl acetate:hexane (1:1 v/v) to give 140 mg of 5-(2-acetamidophenyl)-2,4-dihydro-4-ethyl-1H-[1,2,4]triazol-3-thione, mp 193°–194° C.

The synthesis of additional 5-aryltriazol-3-thiones is described in the following references, all of which are incorporated herein by reference: Deliwala, et al., *J. Med. Chem.*, 13: 672–674 (1970); Rollas, et al., *Pharmazie*, 48(H.4):308–309 (1993); Shah, et al., *J. Pharma. Sci.*, 58(11):1398–1401 (1969); Mhasalkar, et al., *J. Med. Chem.*, 14(5):260–262 (1971); Maxwell, et al., *J. Med. Chem.*, 27:1565–1570 (1984); and Sung, et al., *J. Heterocyclic Chem.*, 29:1101–1109 (1992).

Additional compounds prepared according to the processes thus described include the following Examples 41–61:

| Example | |
|---|---|
| 41 | 5-(2-chlorophenyl)-4-ethyl-2,4-dihydro-[1,2,4]triazole-3-thione, mp 196–197° C. |
| 42 | 5-(4-trifluoromethylphenyl)-4-ethyl-2,4-dihydro[1,2,4]triazole-3-thione, mp 190–191° C. |
| 43 | 5-(4-t-butylphenyl)-4-ethyl-2,4-dihydro-[1,2,4]triazole-3-thione, mp 166–167° C. |
| 44 | 5-(2-aminophenyl)-4-isopropyl-2,4-dihydro-[1,2,4]triazole-3-thione, mp 223–225° C. |
| 45 | 5-(2-aminophenyl)-4-propyl-2,4-dihydro[1,2,4]-triazole-3-thione, mp 162–163° C. |
| 46 | 5-(2-methylphenyl)-4-ethyl-2,4-dihydro[1,2,4]-triazole-3-thione, mp 180–181° C. |
| 47 | 5-(2-amino-4,5-difluorophenyl)-4-ethyl-2,4-dihydro[1,2,4]triazole-3-thione, mp 195–197° C. (decomp). |
| 48 | 5-(3,4-difluorophenyl)-4-ethyl-2,4-dihydro-[1,2,4]triazole-3-thione, mp 156–157° C. |
| 49 | 5-(2-methylsulfanyl-pyridin-3-yl)-4-ethyl-2,4-dihydro[1,2,4]triazole-3-thione, mp 221–222° C. |
| 50 | 5-(2-pyrrol-1-ylphenyl)-4-ethyl-2,4-dihydro-[1,2,4]triazole-3-thione, mp 183–185° C. |
| 51 | 5-(4-hydroxy-5-chloropyridin-3-yl)-4-ethyl-2,4-dihydro[1,2,4]triazole-3-thione, mp > 260° C. |
| 52 | 5-(2-phenoxypyridin-3-yl)-4-ethyl-2,4-dihydro-[1,2,4]triazole-3-thione, mp 198–200° C. |
| 53 | 5-(2-methylphenyl)-4-methyl-2,4-dihydro-[1,2,4]triazole-3-thione, mp 107–108° C. |
| 54 | 5-(2-aminophenyl)-4-H-2,4-dihydro[1,2,4]-triazole-3-thione, mp > 250° C. |
| 55 | 5-(2-phenoxypyridin-3-yl)-4-ethyl-2,4-dihydro-[1,2,4]triazole-3-thione, mp 198–200° C. |
| 56 | 5-(5-chloro-4-hydroxypyridin-3-yl)-4-ethyl-2,4-dihydro[1,2,4]triazole-3-thione, mp > 260° C. |
| 57 | 5-(2-pyrrolephenyl)-4-ethyl-2,4-dihydro-[1,2,4]triazole-3-thione, mp 183–185° C. |
| 58 | 4-ethyl-5-(2-methylsulfanyl-pyrridin-3-yl)-2,4-dihydro[1,2,4]triazole-3-thione, mp 221–222° C. |
| 59 | 5-(3,4-difluorophenyl)-4-ethyl-2,4-dihydro-[1,2,4]triazole-3-thione, mp 156–157° C. |
| 60 | 5-(2-amino-4,5-difluorophenyl)-4-ethyl, mp 185–197° C. (decomp). |
| 61 | 5-(4-nitrophenyl)-4-ethyl-2,4-dihydro[1,2,4]-triazole-3-thione, mp 227-233° C. (decomp). |

The 5-aryltriazol-3-thiones described above have been found to inhibit the leukocyte adhesion molecule Mac-1, and thereby are useful as cytoprotective agents to treat and prevent diseases mediated by the Mac-1 integrin. Cytoprotection as used herein includes protection against damage to the gastrointestinal mucosa by the blockage of prostaglandin biosynthesis.

The role of endothelial adhesion molecules such as Mac-1 has been implicated in a number of human disease states. For example, neutrophil-mediated inflammation has been established as involved in adult respiratory distress syndrome, multi-organ failure, and reperfusion injury. One way to inhibit or treat such inflammatory responses entails competitively blocking the adhesive interactions between neutrophils and the endothelium adjacent to the inflamed region (see Watson, et al., *Nature*, 349:164–167 (1991)). We have now discovered that 5-aryltriazol-3-thiones are effective at blocking the Mac-1 leukocyte adhesion molecule.

Studies have established that neutrophil adherence to the vascular endothelium is a critical early event in the pathogenesis of gastric mucosal injury induced by nonsteroidal anti-inflammatory drugs (NSAIDs) (see Wallace, et al., *Am. J. Physiol.*, 265:G993–G998 (1993)), incorporated herein by reference. A preferred embodiment of this invention is thus treatment of NSAID-induced gastrointestinal lesions and ulcers comprising administering to a subject in need of treatment an amount of a 5-aryltriazol-3-thione effective to inhibit Mac-1 adhesion. Shappell, et al., in *J. of Immunology*, 144:2702–2711 (1990), incorporated herein by reference, established that the Mac-1 leukocyte integrin mediates the adherence-dependent production of hydrogen peroxide, and that inhibition of such adhesion is a viable treatment for myocardial ischemia-reflow injury and results in reduction in infarct size. Another preferred embodiment of this invention is therefore a method of treating ischemia and reperfusion comprising administering to a subject in need of treatment a Mac-1 inhibiting amount of a 5-aryltriazol-3-thione.

Similarly, Simpson, et al., in *Circulation*, 81:226–237 (1990), incorporated herein by reference, confirms that inhibition of Mac-1 adhesion significantly reduces myocardial ischemia. Accordingly, this invention provides a method of treating myocardial ischemia by administering an effective amount of a 5-aryltriazol-3-thione. Mulligan, et al., *J. of Immunology*, 150:2401–2406 (1993), incorporated herein by reference, disclose that inhibition of Mac-1 can diminish the effects of lung injuries resulting from acute inflammatory reactions. The invention therefore provides a method of treating lung disease mediated by Mac-1 by administering to a subject in need of treatment a Mac-1 inhibiting amount of a 5-aryltriazol-3-thione.

We have evaluated the ability of 5-aryltriazol-3-thiones to inhibit Mac-1 adhesion in in vitro and in vivo models recognized and routinely utilized by those skilled in the art. For example, Wallace, et al., *Gastroenterology*, 100:878–883 (1991), describes in vivo studies to measure prevention of adherence of leukocytes to vascular endothelium mediated by several adhesion molecules, one of which is Mac-1. Similarly, Rosen, *J. Leukocyte Biology,* 48:465–469 (1990), incorporated herein by reference, discusses in vivo testing in mice, rabbits, and dogs for determining leukocyte adhesion and inflammatory recruitment.

Protocol for Human Neutrophil Mac-1 Adhesion Assay

We evaluated several 5-aryltriazol-3-thiones utilizing methodology similar to that of Ferrante and Thong as described in *J. Immunol. Methods,* 24:389–393 (1978), and Shappell, et al., *J. Immunol.,* 144:2702–2711 (1990), both of which are incorporated herein by reference. Namely, we utilized Ferrante and Thong's methodology to isolate neutrophils from ethylenediaminetetraacetic acid (EDTA)-treated venous blood obtained from healthy human volunteers. Keyhole limpet hemocyanin (KLH) coated microtiter plates were prepared as follows:

All pipetting was automated using the Cetus Pro/Pette (Perkin-Elmer; division of Applied Biosystems, Foster, Calif.). KLH, Megathura crenulata; Calbiochem-Novabiochem, La Jolla, Calif., was prepared at a concentration of 0.5 mg/mL in Dulbecco's PBS phosphate buffered saline (PBS) with CA++, pH 7.2 (DPBS).

Microtiter plates are prewashed with 50% EtOH for 1 hour at 37° C., then drained and blotted to dryness. Then 0.3 mL KLH solution was pipetted into each well of the 96 well microtiter plate, covered and incubated overnight at 37° C. Plates are then inverted to drain, blotted to dryness, washed with 0.3 mL cold D-PBS, drained, blotted to dryness, then stored at 4° C. until use.

Procedure for PMN KLH (Mac-1 Adhesion Assay)

On the Pro/Pette system, a treatment plate was placed in plate position 1 (P-1), buffer Micro.trof was placed in plate position 2 (P-2), and a single row of tips in a spare magazine are placed in the tip position on the carriage. Two hundred ten μL aliquots D-PBS are pipetted into all wells (105 μL using Cetus File #18, Micro.trof 3, no mixes, tip row H, no tip change, run twice). Drug plate was placed in plate position 2 (P-2). Donor drug plates were prepared to contain buffer or drug in appropriate wells. Thirty μL drug or D-PBS buffer are pipetted into appropriate wells in the treatment plate in position 1 (P-1) (Cetus File #17, one mix before and after, changing tips) from donor plate. Thirty μL of neutrophils (PMNs) (30 μL of $10^7$ cells/mL) were next pipetted from either a Micro.trof 1, position 2 (P-2), or a row of 0.5 mL capacity microcentrifuge tubes (Sarstedt RIA vials) to plate 1 using Cetus File #18, changing tips, one mix (50 μL) before and after. Cells and drug were then incubated for 10 minutes at 37° C. Agonist (e.g., FMLP) or D-PBS buffer (30 μL) were next pipetted to appropriate wells using Cetus File #18 (Micro.trof) or Cetus File #42 (for plate to plate), changing tips and one mix before and after. Cell/drug/agonist mixture was then incubated for 60 minutes at 37° C. After the incubation period, the treatment plate is gently inverted to drain, blotted lightly to dryness on a paper towel. The treatment plate is then washed with 300 μL D-PBS buffer using Cetus File #18, using pump at slow speed, again inverted to drain, and again blotted to dryness. Adherent cells are stained by the addition of 150 μL D-PBS buffer to all wells, using Cetus File #18, Micro.trof 3 no tip change. Then the addition of 150 μL of 0.025% Rose Bengal dye in D-PBS, again using Cetus File #18, Micro.trof 3 no tip change. The treatment plate is then incubated overnight at 37° C.

After overnight incubation, the treatment plate is gently inverted to drain, blotted to dryness on paper towel, then gently washed with 300 μL D-PBS buffer using Cetus File #18, using pump at slow sped. The treatment plate is then gently inverted to drain, and blotted to dryness. The washing of the treatment plate is repeated until all excess dye is removed.

To develop the dye color, 150 μL 50% EtOH is added to each well of the treatment plate using Cetus File #18, Micro.trof 3, no mixes, no tip change. The treatment plate is then covered and incubated for 60 minutes at 37° C. After the incubation, 150 μL 50% EtOH is added to each well of the treatment plate using Cetus File #18, Micro.trof 3, mixing three times, changing tips. Optical densities (ODs) for the wells of the treatment plate are read using a Titertek Multiskan(R) MCC/340 microtiter plate reader with absorbance wavelength 570 nm (Rose Bengal), then data is either read from a thermal printout tape or sent directly to a Lotus 123 file. Data Calculations (Lotus 123 spreadsheet):

a. mean unstimulated cell control OD is determined and subtracted from all other values b. mean net stimulated, e.g., FMLP, control values are determined c. mean drug values are determined and percent drug inhibition vs. stimulus control are calculated as follows:

Percent Inhibition =

$$\frac{(OD \text{ stimulated control} - OD \text{ unstimulated control}) - (OD \text{ treated} - OD \text{ unstimulated control})}{(OD \text{ stimulated control} - OD \text{ unstimulated control})} \times 100$$

d. $IC_{50}$ determinations, plotting logdose vs. percent inhibition, are determined by linear regression analysis using the least squares method.

Protocol for Cytoprotection Studies

For all studies, random-bred, barrier-raised, SPF, female Sprague-Dawley rats (Charles River Laboratories, Portage, Mich.) weighing 180–300 g were used. Animals were acclimated for at least 1 week prior to the studies and housed in wire bottom cages supplied with macrofiltered fresh tap water and Purina Rat Chow #5012 (Purina Mills Inc., Richmond, Ind.) ad libitum. The animal rooms were kept at 22° C.±1° C. and 50% humidity.

All animals were food fasted for 24 hours and water deprived for 2 or more hours prior to treatment administration. For oral dosing, Aspirin (acetylsalicylic acid, Sigma, St. Louis, Mo.) was dissolved in an aqueous solution of 150 mM HCl (Takeucvhi K., *Digestive Disease and Science,* 35:178–185 (1990)). Misoprostol was used as a standard. The test compound was dissolved in double glass distilled water, normal saline USP (NS) or the misoprostol phosphate buffer vehicle. All oral doses of misoprostol and test compounds were administered in a volume of 1 mL/animal. All oral dosing was done by gavage using a 3 mL syringe attached to a 25 inch, 17 gauge gavage needle.

The test compounds were administered in 1 mL 15 minutes prior to treatment with an oral dose of acidified aspirin (288 mg/kg in 150 mM HCl) given in 1 mL. Stomachs were removed to assess gastric damage 30 minutes after exposure to the damaging agent. The stomach was isolated through a midline incision in the abdomen followed by clamping of the esophagus and duodenum. Seven milliliters of 10% formalin (Fisher Scientific, Fair Lawn, N.J.) was injected into the stomach which was then excised and submerged in formalin for at least 10 minutes. The stomach was then opened along the greater curvature and pinned flat and submerged in formalin overnight. After the forestomach and exterior blood vessels were trimmed away, the tissues were clarified with glycerol (E. M. Science, Gibbstown, N.J.) and flattened between Plexiglass plates. Gastric damage was measured with a Cambridge Instruments LTD., (Cambridge, UK) Quantimet 970 Image Analysis System. Hemorrhagic damage appeared as darkened areas on a background of lighter undamaged tissue. This darker area was detected and surface area measured by the image analyzer. In addition, the complete stomachs were also completely submerged in 0.1N solution of iodine (J. T. Baker Chemical Co., Phillipsburg, N.J.), and the total stomach surface area was determined. The system was calibrated prior to each use with a standard sample. The percent damage and percent protection was computed by the following equation:

$$\% \text{ Damage} = \frac{\text{Surface area of stomach damaged}}{\text{Total surface of stomach}} \times 100$$

$$\% \text{ Protection} = \frac{\text{Average \% damage in vehicle treated} - \% \text{ damage in drug treated}}{\text{Average \% damage in vehicle treated}} \times 100$$

Results of the above assay are presented in Table I for representative 5-aryltriazol-3-thiones.

TABLE I

| Example | Ar | $R_4$ | Mac-1 KLH Assay $IC_{50}$ or % Inhibition @ 33 μM | Cytoprotection % Inhibition (1 mg/kg PO) |
|---|---|---|---|---|
| 2 | 4-$NH_2C_6H_4$ | Et | 36.9% | |
| 4 | 4-$OHC_6H_4$ | Et | 7.8 | |
| 5 | 2-$OHC_6H_4$ | Et | 4.3 | |
| 6 | 2-$NH_2$,5-$ClC_6H_3$ | Et | 0.8 | 55.12 |
| 7 | 2-$NH_2$, 4,5-di-$OCH_3C_6H_2$ | Et | 7.1 | |
| 11 | 4-$OCH_3C_6H_4$ | Et | 1.6 | 32.23 |
| 12 | 2,4-$diClC_6H_3$ | Et | 2.1 | 59.38 |
| 16 | 3,4-$diOCH_3C_6H_3$ | Et | 3.1 | 62.2 |
| 22 | 2-$CH_3C_6H_4$ | Ph | 0.2 | |
| 23 | $C_6H_5$ | Ph | 1.1 | 21.4 |
| 24 | 2-$OCH_3C_6H_4$ | Ph | 2.5 | |
| 25 | $C_6H_5$ | $CH_2Ph$ | 8.1 | |
| 26 | 3,4-di-$OCH_3C_6H_3$ | Ph | 0.8 | |
| 27 | 4-$OHC_6H_4$ | Ph | 6% | |
| 28 | 3-$OCH_3C_6H_4$ | Ph | 60% | |
| 29 | 4-$OHC_6H_4$ | $CH_2Ph$ | 42% | |
| 31 | 4-$NH_2C_6H_4$ | Ph | 15% | |
| 32 | 3,4-di-$OCH_3C_6H_3$ | $CH_3$ | 1.5 | 21.65 |
| 33 | 4-$OCH_3C_6H_4$ | Ph | 4.1 | |
| 34 | $C_6H_5$ | H | 58% | |
| 35 | 2-$NH_2C_6H_4$ | Ph | 24% | |
| 36 | 2-$NH_2C_6H_4$ | Et | 0.4 | 53.74 |
| 37 | 2-$NHCH_3C_6H_4$ | Ph | 7% | |
| 38 | 2-$NH_2C_6H_4$ | $CH_3$ | −0.1% | 51.25 |
| 39 | 2-$NH_2C_6H_4$ | $NH_2$ | 57% | |

The foregoing data establish that 5-aryltriazol-3-thiones effectively inhibit Mac-1 mediated diseases such as inflammatory gastritis and ulceration, ischemia, reperfusion, ulcerative colitis, inflammatory bowel disease, and multiple sclerosis. The compounds will be formulated with standard pharmaceutical excipients, carriers and diluents for convenient administration via the oral or parenteral routes. For oral administration, the compounds will be formulated into solid or liquid preparations such as tablets, capsules, solutions, suspensions, or sustained release compositions with polymers, oils, waxes, and the like. Typical formulations will contain about 10% to about 90% of the 5-aryltriazol-3-thiones by weight. For parenteral administration, the compounds will be made into solutions or suspensions by admixing with carriers such as water, isotonic saline, 5% aqueous glucose, ethanol, mineral oil, propylene glycol, polyethylene glycol, and the like. The compounds will be administered at doses which are effective to inhibit Mac-1 adhesion, and are thus effective to treat the disease mediated thereby, such as NSAID-induced gastrointestinal lesions and ulcers. Typical doses for such treatments will be from about 0.5 to about 50 mg per kg of body weight, and ideally from about 1 to about 10 mg/kg.

We claim:

1. A method of inhibiting the adhesion of Mac-1 to endothelial cells, the method comprising administering to a subject having NSAID-induced gastritis, inflammatory bowel disease of ulcerative colitis a Mac-1 inhibiting amount of a compound of the formula

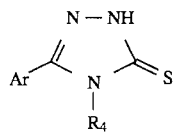

wherein

Ar is phenyl, pyridyl, naphthyl, and flurenyl, each of which may be mono-, di-, trisubstituted; and $R_4$ is hydrogen, amino, hydroxy, alkyl, alkenyl, cycloalkyl, phenyl or substituted phenyl, benzyl or substituted benzyl, and the pharmaceutically acceptable addition salts thereof.

2. The method of claim 1 wherein the compound administered is

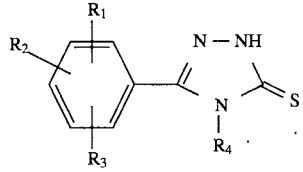

wherein:

$R_1$, $R_2$, and $R_3$ independently are hydrogen, hydroxy, $C_1$–$C_4$ alkyl, $C_1$–$C_4$ alkoxy, $C_1$–$C_4$ alkylthio, nitro, amino, $C_1$–$C_4$ alkylamino, di-$C_1$–$C_4$ alkylamino, $C_1$–$C_4$ alkanoylamino, phenoxy, trifluoromethyl, 1-pyrrolo, $N(CH_2)_n$ where n is 3, 4, 5, or 6, or halo;

$R_4$ is hydrogen, $C_1$–$C_4$ alkyl, $C_2$–$C_4$ alkenyl, $C_3$–$C_6$ cycloalkyl, amino, hydroxy, $C_1$–$C_4$ alkylamino, di-$C_1$–$C_4$ alkylamino, phenyl, substituted phenyl, benzyl or substituted benzyl.

3. The method of claim 2 wherein $R_4$ is $C_1$–$C_4$ alkyl.

4. The method of claim 3 wherein $R_4$ is methyl or ethyl.

5. The method of claim 4 wherein $R_1$ is hydrogen.

6. The method of claim 5 wherein $R_2$ and $R_3$ independently are hydrogen, hydroxy, methoxy, amino, or halo.

7. The method of claim 2 wherein $R_4$ is phenyl or benzyl.

8. The method of claim 2 wherein $R_4$ is hydrogen.

9. The method of claim 1 wherein the subject has NSAID-induced gastritis.

10. The method of claim 1 wherein the subject has inflammatory bowel disease.

11. The method of claim 1 wherein the subject has ulcerative colitis.

* * * * *